US012765839B1

(12) United States Patent
Ehrlich

(10) Patent No.: US 12,765,839 B1
(45) Date of Patent: Oct. 20, 2026

(54) METHODS AND DEVICES FOR INCREASING AWARENESS TO SELF-HEARTBEATS

(71) Applicant: Gal Ehrlich, Tel-Aviv (IL)

(72) Inventor: Gal Ehrlich, Tel-Aviv (IL)

( * ) Notice: Subject to any disclaimer, the term of this patent is extended or adjusted under 35 U.S.C. 154(b) by 0 days.

(21) Appl. No.: 19/454,482

(22) Filed: Jan. 21, 2026

(51) Int. Cl.
*A61B 5/00* (2006.01)
*G16H 20/00* (2018.01)

(52) U.S. Cl.
CPC ........... *A61B 5/6843* (2013.01); *G16H 20/00* (2018.01)

(58) Field of Classification Search
CPC .............................. A61B 5/6843; G16H 20/00
See application file for complete search history.

(56) References Cited

U.S. PATENT DOCUMENTS

| | | | | |
|---|---|---|---|---|
| 10,532,181 | B2 * | 1/2020 | Hooper | A61B 5/486 |
| 2019/0307983 | A1 * | 10/2019 | Goldman | A61B 5/165 |
| 2025/0143644 | A1 | 5/2025 | Lin et al. | |
| 2025/0176834 | A1 | 6/2025 | Connor | |

FOREIGN PATENT DOCUMENTS

| | | |
|---|---|---|
| CN | 120766975 | 10/2025 |

OTHER PUBLICATIONS

“Abdallah El Ali, Rayna Ney, Zeph M. C. van Berlo, Pablo Cesar, Is that my Heartbeat? Measuring and Understanding Modality-dependent Cardiac Interoception in Virtual Reality, Sep. 29, 2023, IEEE” (Year: 2023).*

“André Schulz, Claus Vögele, Interoception and stress, Jul. 20, 2015, frontiers in Psychology”. (Year: 2015).*

* cited by examiner

*Primary Examiner* — Carl H Layno
*Assistant Examiner* — Aya Ziad Bakkar

(57) ABSTRACT

Embodiments of the invention provide for methods, devices and systems, which cause relaxation through promoting heartbeat awareness. The invention relates to a method of increasing perception of self-heartbeats by a user by mounting a wearable device against a pulse point of the user and applying pressure at a level sufficient to augment transfer of arterial pulsations according to self-heartbeats.

20 Claims, 9 Drawing Sheets

METHODS AND DEVICES FOR INCREASING AWARENESS TO SELF-HEARTBEATS

FIELD AND BACKGROUND OF THE INVENTION

The present invention, in some embodiments thereof, relates to methods and devices for increasing awareness to self-heartbeats.

In today's fast-paced world, stress and anxiety have become prevalent issues affecting individuals' overall well-being. The physiological response to stress can manifest in various ways, including elevated heart rate, increased blood pressure and heightened tension, which can negatively impact both mental and physical health. Traditional methods for managing stress often include practices such as meditation, deep breathing exercises and physical activity. However, these methods require time and consistent practice, which may not be feasible for everyone in their daily routines.

Biofeedback is a therapeutic technique that utilizes electronic monitoring to convey information about physiological processes, enabling individuals to gain voluntary control over these processes. By providing real-time feedback on physiological parameters such as heart rate variability and respiration, biofeedback can help individuals manage stress and improve relaxation.

Recent advancements in wearable technology have led to the development of smart devices such as smartwatches and fitness trackers. These devices are equipped with sensors to monitor physiological parameters, offering users insights into their health metrics. Such devices are disclosed in CN120766975, US20250143644 and US20250176834.

SUMMARY OF THE INVENTION

Example 1. A wearable device for increasing perception of self-heartbeats by a user, comprising:

(i) a body sized and shaped for mounting against a pulse point of the user, said body including:
 (a) at least one integrated deforming section;
(ii) a regulator which regulates said deforming section to cause said body to apply controlled pressure such that the user perceives the self-heartbeats over a predetermined period of time Example 1.1 The device of example 1, wherein the regulator regulates said deforming section over said predetermined period of time.

Example 1.2 The device of any one of Examples 1-1.1, wherein said controlled pressure is of at least 5 mmHg and/or is for a time period exceeding 20 seconds.

Example 2. The device of any one of examples 1-1.2, further comprising a power source for operating at least one of said regulator and said deforming section.

Example 3. The device of example any one of examples 1-2, wherein said deforming section comprises at least one actuator selected from the group consisting of a pneumatic chamber, a hydraulic chamber and a shape memory alloy actuator.

Example 4. The device of any one of examples 1-3, further comprising at least one sensor.

Example 5. The device of example 4, wherein said at least one sensor comprises a safety sensor configured to detect blood flow at said pulse point and to provide data of said blood flow to said regulator for real-time adjustment of said controlled pressure.

Example 6. The device of example 4 or 5, wherein said at least one sensor comprises a physiological sensor.

Example 7. The device of example 6 wherein said physiological sensor is configured to detect a physiological signal of the user and to provide physiological data to said regulator.

Example 8. The device of example 7, wherein said regulator adjusts said controlled pressure based on said physiological data and/or said physiological signal.

Example 9. The device of example 7, wherein said regulator is configured to regulate said pressure in response to physiological data received from said physiological sensor.

Example 10. The device of example 7 or 8, wherein said physiological signal is selected from the group consisting of heartbeat, respiration, heart rate variability, blood pressure and blood pressure variability.

Example 11. The device of any one of examples 4-10, wherein said at least one sensor comprises a device operability sensor, which generates a signal indicating proper mounting of said body at a skin region comprising said pulse point.

Example 12. The device of any one of examples 1-11, comprising a user interface (UI) for receiving external information from the user.

Example 13. The device of example 12, wherein said external information is selected from the group consisting of stress level, preference for duration of said controlled pressure appliance and environmental conditions.

Example 14. The device of example 12 or 13, wherein said UI comprises a control element for pressure adjustment by said user.

Example 15. The device of any one of examples 1-13, further comprising an actuator that generates a human perceptual signal corresponding to said self-heartbeats.

Example 16. The device of example 15, wherein said human perceptual signal is selected from the group consisting of an acoustic signal, a haptic signal, an optical signal and a combination of two or more of said signals.

Example 17. The device of any one of examples 1-16, wherein said body comprises a decompression section which comprises a circuitry controlled by said regulator in response to said regulator receiving a signal from said sensor and/or said user.

Example 18. The device of example 17, wherein said decompression circuitry is a mechanical circuitry.

Example 19. The device of example 17, wherein said decompression circuitry is an electronic circuitry Example 20. The device of any one of examples 1-19, wherein said regulator comprises a calibration mode configured for determining a personalized range of said controlled pressure based on at least one of a user preference and a safety parameter comprising blood flow.

Example 21. The device of example 20, wherein said user preference is based on pain threshold of said user;

Example 22. The device of example 20, wherein said user preference is based on pleasure feeling of said user in response to said pressure.

Example 23. The device of any one of examples 1-17, wherein said regulator is configured to vary said controlled pressure over time.

Example 24. The device of any one of examples 1-18, wherein said wearable is selected from the group consisting of a thumb or finger cover, a wristband and a patch configured for positioning over a pulse point of the user.

Example 25. The device of any one of examples 1-24, wherein said pulse point is selected from the group consisting of a thumb, a finger, a wrist, an ankle and a temple.

Example 26. A non-transitory computer-readable medium storing instructions that, when executed by at least one processor, cause the processor to:

(a) communicate with a device configured to apply pressure to a pulse point;

(b) determine a variation in pressure to be applied by said device;

(c) convert said determined variation into control commands for said device; and (d) wirelessly transmit the control commands to the device, to control operation thereof.

Example 27. The non-transitory computer-readable medium of example 26, wherein the at least one processor is comprised in a mobile communication device.

Example 28. The non-transitory computer-readable medium of example 26, wherein the at least one processor is comprised in a remote server configured to communicate with the device via a network.

Example 29. A method for controlling application of pressure to a pulse point of a user, the method comprising, by at least one processor of a computing device:

(a) communicating with a wearable device configured to apply pressure to a pulse point;

(b) determining a variation in pressure to be applied by said device;

(c) converting said determined variation into control commands for said device; and (d) wirelessly transmitting the control commands to the device, to control operation thereof.

Example 30. The method of example 29, wherein the at least one processor is comprised in a mobile communication device.

Example 31. The method of example 29, wherein the at least one processor is comprised in a remote server configured to communicate with the device via a network.

Example 32. An apparatus for controlling application of pressure to a pulse point of a user, comprising:

(i) at least one processor;

(ii) a memory coupled to the at least one processor and storing instructions; and (iii) a wireless communication module operatively coupled to the at least one processor and configured to wirelessly communicate with a device configured to apply pressure to a pulse point;

wherein the instructions, when executed by the at least one processor, cause the at least one processor to:

(a) communicate, via the wireless communication module, with the device configured to apply pressure to the pulse point;

(b) determine a variation in pressure to be applied by said device;

(c) convert said determined variation into control commands for said device; and (d) wirelessly transmit, via the wireless communication module, the control commands to the device, to control operation thereof.

Example 33. The apparatus of example 32, wherein the apparatus comprises a mobile communication device.

Example 34. The apparatus of example 32, wherein the apparatus comprises a remote server configured to communicate with the device via a network.

Example 35. The medium, method or apparatus of any one of examples 26-34, wherein communicating with the device configured to apply pressure to the pulse point comprises establishing a wireless communication link using at least one protocol selected from the group consisting of Bluetooth, Bluetooth Low Energy (BLE), Wi-Fi, and a cellular communication protocol.

Example 36. A method of increasing perception of self-heartbeats by a user, the method comprising:

mounting a wearable device against a pulse point of the user, said wearable device comprising a pressure applicator;

using said device to apply said controlled pressure at a level sufficient to augment transfer of arterial pulsations corresponding to the self-heartbeats from an artery to a sensing nerve of the user and improve the perception of self-heartbeats by the user without causing substantial blood occlusion.

Example 37. A method of promoting relaxation of a user, the method comprising:

mounting a wearable device against a pulse point of the user, said wearable device comprising a pressure applicator;

using said device to apply said controlled pressure at a level sufficient to augment transfer of arterial pulsations corresponding to the self-heartbeats from an artery to a sensing nerve of the user and improve the perception of self-heartbeats by the user without causing substantial blood occlusion, thereby promoting relaxation of the user.

Example 38. The method of example 36 or 37, wherein said level comprises at least 5 mmHg optionally for a time period exceeding 60 seconds.

Example 39. The method of any one of examples 36-38, further comprising determining a stress level of the user prior to and or following applying.

Example 40. The method of example 39, further comprising adjusting said level of said controlled pressure based on said stress level.

Example 41. The method of any one of examples 36-40, wherein said level of said controlled pressure avoids pain sensation while said applying.

Example 42. The method of any one of examples 36-41, further comprising directing attention of the user to a tactile sensation produced by said controlled pressure.

Example 43. The method of example 42, wherein said directing attention is by an audio signal, optical signal and/or haptic signal.

Example 44. The method of any one of examples 36-43, wherein said applicator is operated by the user.

Example 45. The method of any one of examples 36-43, wherein said device is automatically operated.

Example 46. The method of any one of examples 36-45, wherein said promoting relaxation is for acute-stress release.

Example 47. The method of any one of examples 36-45, wherein said promoting relaxation is for ongoing wellness maintenance.

Example 48. The method of any one of examples 36-44, wherein said skin region comprises a pulse point.

Example 49. The method of any one of examples 36-48, wherein said pulse point is selected from the group consisting of a thumb, a finger, a wrist, an ankle and a temple.

Example 50. The method of any one of examples 36-49, further comprising monitoring the arterial pulsations and optionally adjusting said level of controlled pressure based on the monitored arterial pulsations.

Example 51. The method of any one of examples 36-50, further comprising reducing said level of said controlled pressure if a pre-determined level of relaxation is reached and/or an indication of the blood flow occlusion is indicated.

Example 51.1 The method of any one of examples 36-51, wherein step (b) is carried out at least in part under control of an application downloadable from an application store or application marketplace optionally executable on a computing platform associated with the wearable device, the application being configured to control one or more operating parameters of the pressure applicator.

Example 51.2 The method of example 36, wherein said wearable device comprises:

(i) a body sized and shaped for mounting against a pulse point of the user, said body including:
at least one integrated deforming section;

(ii) a regulator which regulates said deforming section to cause said body to apply controlled pressure such that the user perceives the self-heartbeats over a predetermined period of time.

Example 51.3 The method of example 51.2, wherein said deforming section comprises at least one actuator selected from the group consisting of a pneumatic chamber, a hydraulic chamber and a shape memory alloy actuator.

Example 51.4 The method of example 51.2, wherein said device comprises at least one sensor selected from the group consisting of a safety sensor, a physiological sensor and an operability sensor.

Example 51.5 The method of example 51.4, wherein said regulator is configured to regulate said pressure in response to physiological data received from said physiological sensor.

Example 51.6 The method of example 51.2, wherein said device further comprises an actuator that generates a human perceptual signal corresponding to said self-heartbeats.

Example 51.7 The method of example 51.2, wherein said body comprises a decompression section which comprises a circuitry controlled by said regulator in response to said regulator receiving a signal from said sensor and/or said user.

Example 51.8 The method of example 51.2, wherein said regulator comprises a calibration mode configured for determining a personalized range of said controlled pressure based on at least one of a user preference and a safety parameter comprising blood flow.

Example 52. A method of calibrating a device for increasing perception of self-heartbeats by a user, the method comprising:

mounting a wearable device against a pulse point of the user, said wearable device comprising a pressure applicator;

using said system to apply pressure at said pulse point to augment transfer of arterial pulsations corresponding to self-heartbeats from an artery to a sensing nerve of the user;

determining a level of pressure sufficient for the user to perceive said self-heartbeats without causing substantial blood occlusion, said level of pressure can be used in a method of increasing relaxation of the user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer and may not be feasible or practical for performing purely manually, by a human expert. A human expert who wanted to manually perform similar tasks, such as planning or guiding a procedure, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 5A:
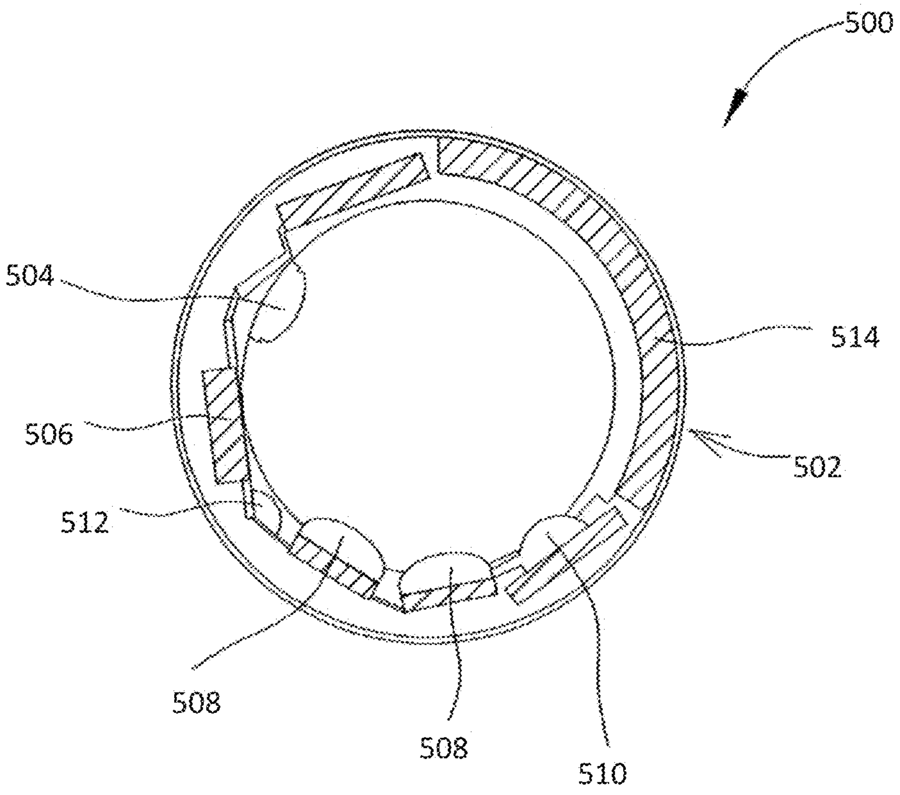
Figure 5B:
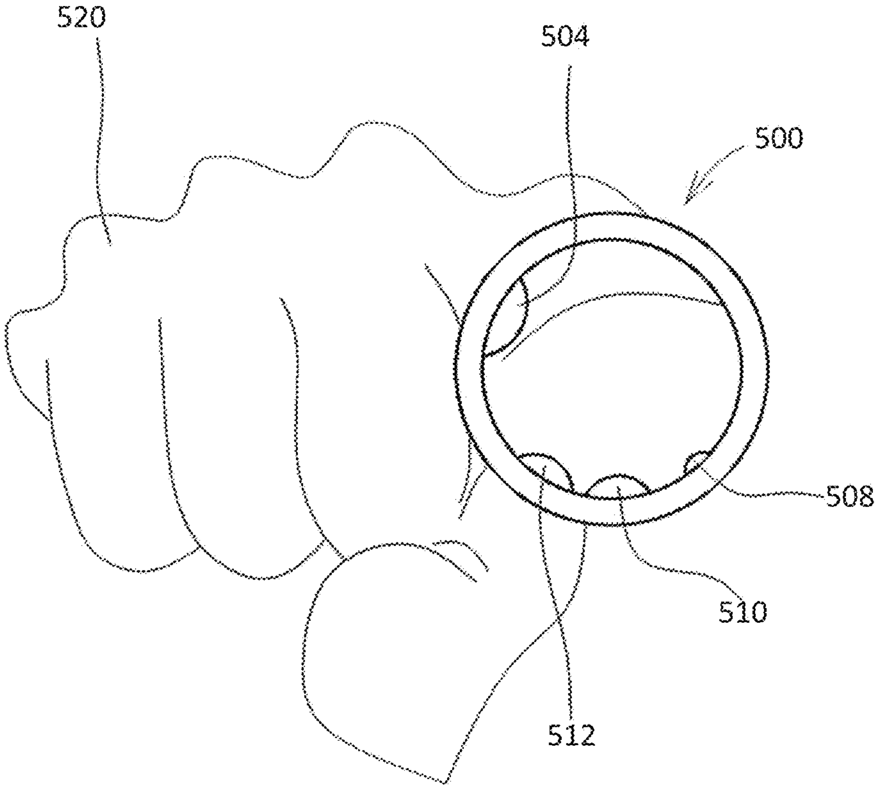
Figure 6:
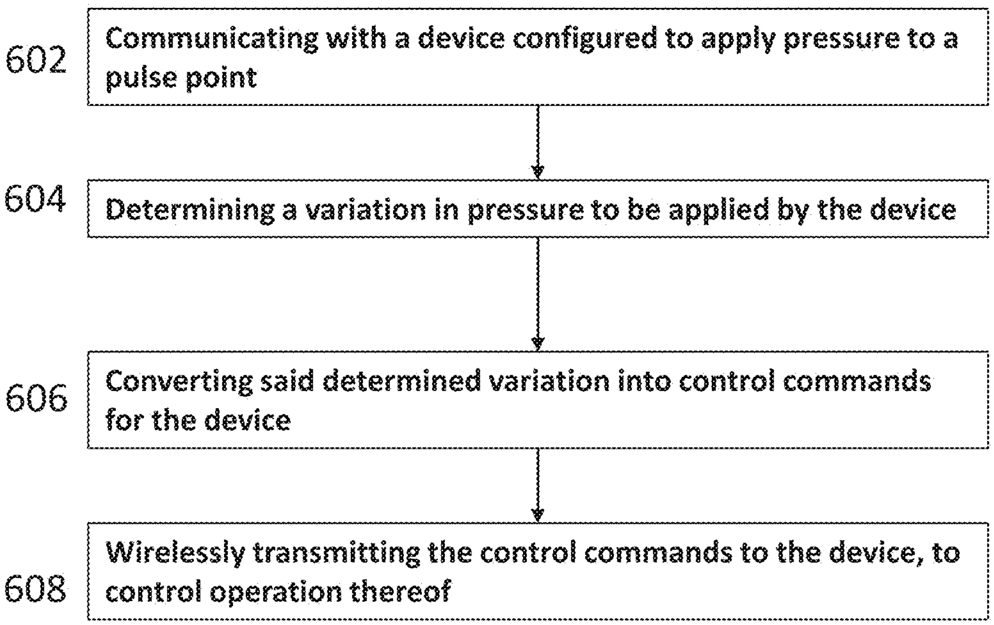
Figure 7:
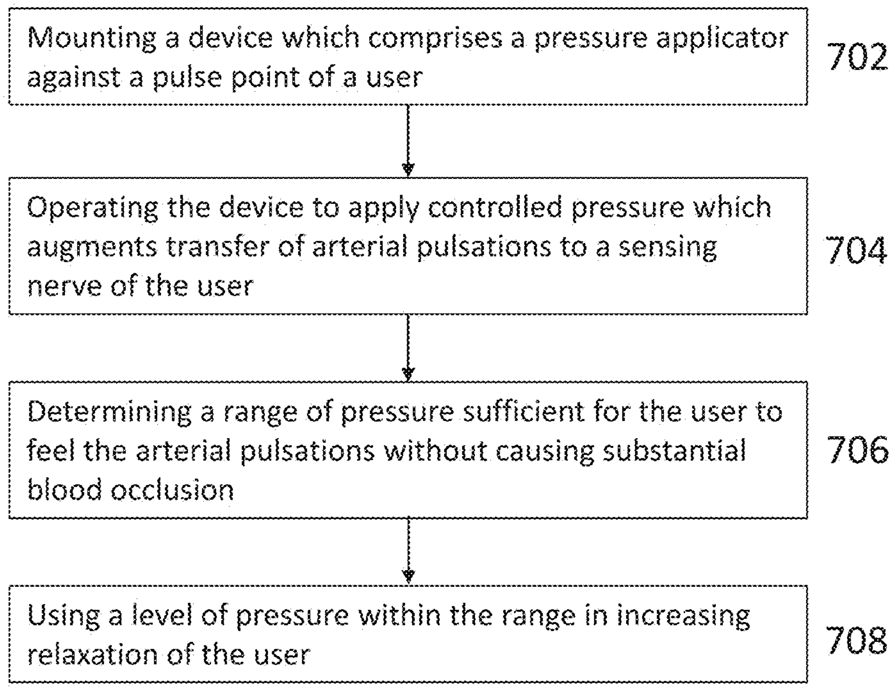
Figure 8:
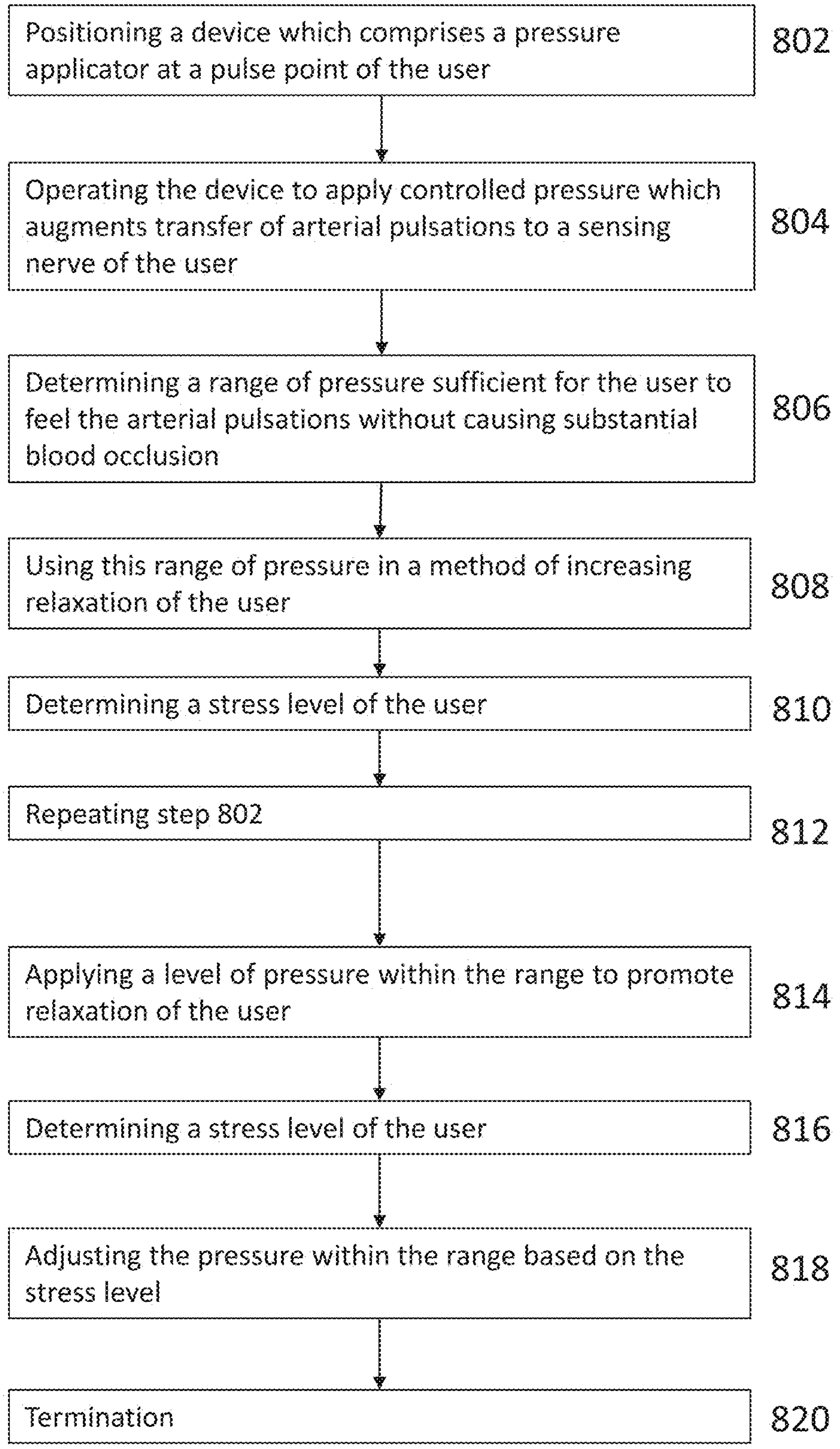

FIGS. 3A-F are illustrations of pulse points and mounted wearables for increasing perception of self-heartbeats, according to some embodiments of the invention;

FIGS. 4A-D are illustrations of wearables for increasing perception of self-heartbeats by a user, according to some embodiments of the invention;

FIGS. 5A-B illustrate a ring and a cross section of a mounted ring for increasing perception of self-heartbeats by a user, according to some embodiments of the invention;

FIG. 6 is a flow chart describing instructions stored by a non-transitory computer-readable medium according to some embodiments of the invention;

FIG. 7 is a flow chart describing a calibration method according to some embodiments of the invention;

FIG. 8 is a flow chart describing a method of increasing perception of self-heartbeats by a user according to some embodiments of the invention.

DESCRIPTION OF SPECIFIC EMBODIMENTS OF THE INVENTION

The present invention, in some embodiments thereof, relates to methods and devices for increasing awareness to self-heartbeats.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview

In today's high-pressure global environment, stress and anxiety have become pervasive issues that significantly impact individuals' health and well-being. While various methods exist for managing stress, including meditation, exercise and therapy, these approaches can be time-consuming and may not seamlessly integrate into the fast-paced modern lifestyle. Furthermore, current wearable technologies, such as smartwatches and fitness trackers, primarily serve as diagnostic tools, providing users with valuable health metrics without offering active therapeutic intervention to alleviate stress. Consequently, there remains a need for innovative solutions that not only monitor physiological signals but also actively promote relaxation through direct physiological engagement.

Embodiments of the invention provide for methods, devices and systems, which cause relaxation through promoting heartbeat awareness.

In one embodiment, the invention relates to a wearable device for increasing perception of self-heartbeats by a user, comprising:

(i) a body sized and shaped for mounting against a pulse point of the user, said body including:
  (a) at least one integrated deforming section;
(ii) a regulator which regulates said deforming section to cause said body to apply controlled pressure such that the user perceives the self-heartbeats over a predetermined period of time Specifically, some embodiments of the invention relate to wearable devices that enhance a user's perception of their own heartbeats by applying controlled, localized tactile stimulation such as pressure at an anatomical pulse point and in some embodiments, further relates to methods of using such devices for relaxation, stress modulation and/or individualized calibration.

In one embodiment, a wearable device includes a body sized and shaped to be mounted or worn against a pulse point of a user, such as on a thumb, finger, wrist, ankle, or temple. According to some embodiments, the body incorporates at least one integrated deforming section configured to elicit pressure against the skin region over the pulse point. According to some embodiments, the device comprises a regulator which controls this deforming section so that the device applies a controlled pressure of at least about 5 mmHg at the pulse point and maintains that pressure, or variations thereof, for an extended period, such as of several heartbeats, optionally to allow human time to sense, for example, exceeding about 60 seconds. It is believed that pressure when provided for sufficient time assists in transmitting arterial pulsations from an underlying artery to nearby sensory nerves in the skin, thereby increasing the perceptibility of self-heartbeats without producing substantial blood occlusion.

In some embodiments, deformation of the deforming section may be implemented using one or more actuators, such as pneumatic or hydraulic chambers or shape-memory alloy elements, or a screw, which deform the body to exert the desired pressure on the pulse point.

In some embodiments, the device is powered, for example by an onboard power source that can be used to empower the regulator and/or the deforming section and/or other components of the device.

In further embodiments, the device incorporates one or more sensors. These may include a safety sensor, which detects one or more parameters indicative of safe operation of the wearable device and, optionally, provides corresponding sensor data to a regulator, such that the regulator can prevent, limit, or terminate device operation when predetermined safety criteria are not met. According to some embodiments, the safety sensor is configured to detect blood flow at the pulse point and provide corresponding data to the regulator. The regulator can use this information in real time to adjust the applied pressure to avoid excessive compression or occlusion. According to some embodiments, additional or alternative sensors, or a single sensor can be used for multiple purposes.

According to some embodiments, there is provided a physiological sensor that detects a physiological signal of the user, for example, heartbeat, respiration, heart rate variability, blood pressure and/or blood pressure variability. Data from these sensors can be supplied to the regulator to adapt the pressure, its level, timing, and/or pattern, in response to the user's physiological state. For instance, the pressure pattern may be modulated according to changes in respiration or heart rate variability or synchronized with heartbeats.

According to some embodiments, the sensor, which indicates if the device is properly operable may include, which indicates whether the device is properly mounted at the pulse point. According to some embodiments, a device-operability sensor can detect, for example, contact quality, pressure, and/or positional alignment. According to some embodiments, the sensor can provide information which enable or inhibit operation accordingly, ensuring that the device functions only when correctly applied.

In some embodiments, the device includes a user interface through which the user can provide external input. According to some embodiments, this input may include, for example, an indication of current stress level, preferences regarding the duration of pressure application, and/or information about ambient or environmental conditions. According to some embodiments, the user interface may also provide a control element that allows the user to adjust the applied pressure within predetermined safe limits, enabling a degree of manual customization over intensity and feel.

According to some embodiments, the device may include an actuator that generates a perceptual signal corresponding to the user's heartbeats. This perceptual signal may be acoustic, haptic, optical, or a combination of these modalities. For example, the device may vibrate, emit sounds, or change light output in synchrony with the user's heartbeats or with the pressure pattern.

According to some embodiments, the actuator may reinforce the user's perception of their heartbeat.

According to some embodiments, the actuator may support interoceptive awareness training or relaxation techniques.

In some embodiments, the body of the device further includes a decompression function.

According to some embodiments, the decompression function can be via a decompression circuitry. According to some embodiments, the decompression circuitry, is arranged to release or reduce pressure in response to signals from the one or more sensors and/or from user input. According to some embodiments, the circuitry may be mechanical (e.g., a valve, lever, or spring-based release mechanism) or electronic (e.g., electronically controlled valves, motors, or switches). This allows for automated, controlled pressure reduction when certain conditions are met, such as reaching a target relaxation state and/or detecting signs of excessive compression and/or impending blood occlusion.

According to some embodiments, the regulator may have a calibration mode that determines a personalized range of controlled pressure. In such embodiments, the device conducts a calibration procedure with the user wearing the device at a pulse point. The regulator controls the pressure while optionally, monitoring or asking for user's feedback and, optionally, measured blood flow or other safety parameters. According to some embodiments, through this process, the calibration mode can determine pressure levels that are sufficient to enhance heartbeat perception without causing substantial blood occlusion and that are acceptable from a subjective standpoint. User preferences may be taken into account based on reported pain thresholds and/or, alternatively or additionally, on pleasurable or comfortable sensations produced by the pressure. These individualized parameters can then be stored and used during subsequent operation to deliver safe and effective stimulation tailored to each user.

In some embodiments, the regulator is configured to vary the controlled pressure over time, either according to a pre-defined pattern or dynamically based on sensor input, user input and/or calibration results. Time-varying pressure can enhance the perceptual salience of the arterial pulsations, minimize sensory adaptation, reduce desensitization and/or create massaging or rhythmic patterns aligned and/or intentionally misaligned with the user's intrinsic heart rhythm.

The invention, in some embodiments thereof also encompasses methods of using such a wearable device to increase a user's perception of self-heartbeats and/or promote relaxation. According so some embodiments, the wearable device, including its pressure applicator, is mounted against a pulse point (or in close enough proximity to a pulse point) of the user. According to some embodiments, the device is then operated to apply controlled pressure at a level sufficient to augment transmission of arterial pulsations from an artery to a sensing nerve, optionally a nerve found in the skin. According to some embodiments, the controlled pressure improves perception of the user's own heartbeats while avoiding substantial occlusion of blood flow. According to some embodiments, the pressure level is low enough to be non-occlusive and comfortable for sustained use; is different from the pressure regimes of diagnostic blood pressure cuffs and tonometers; and/or distinguishable from trivial resting contact (e.g., a loose strap or light touch).

Embodiments of the invention also relate to software, methods and apparatus (for example, a smartphone or other computing device) configured to operate a device comprising pressure applicator of some embodiments of the invention.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Increasing Perception of Self-Heartbeats by a User According to Some Embodiments of the Invention Embodiments of the invention rely on an approach which leverages the innate connection between physiological awareness and relaxation responses. Without being bound by theory it is suggested that by enhancing the user's perception of their own heartbeat, it is possible to arrive at a state of attention and focus that naturally encourages relaxation. Other embodiments of the invention rely on an approach that by sensing self-heartbeats one becomes more focused at this physiological activity rather than surrounding thereby promoting relaxation.

Figure 1:
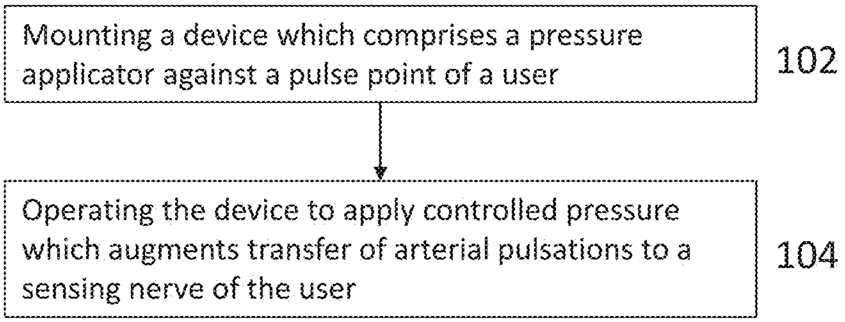
FIG. 1 is a flow chart describing a method of increasing perception of self-heartbeats by a user according to some embodiments of the invention.

Reference is now made to FIG. 1, which describes a method of increasing perception of self-heartbeats by a user.

Mounting a wearable device, which comprises a pressure applicator against a pulse point of the user, is referred to, according to some embodiments, at block 102.

According to some embodiments of the invention, the mounting step is performed by the user placing the wearable device on a body location where the arterial pulsations are naturally palpable and securing the wearable device so that the pressure applicator is in stable contact with the skin.

According to some embodiments of the invention, the method further includes using the wearable device to apply a controlled pressure at a level sufficient to augment transfer of arterial pulsations corresponding to the self-heartbeats from the underlying artery to a sensing nerve of the user, as referred to in block 104.

According to a specific embodiment, the wearable device may be mechanically or electronically operated or a hybrid device comprising mechanical and electronic components.

According to some embodiments of the invention, the controlled pressure is selected so as not to cause substantial blood occlusion at the pulse point, such that arterial blood flow through the artery, and optionally, any other blood vessel, remains substantially unobstructed while the user's feeling (tactile perception) of the pulsations is enhanced.

According to some embodiments of the invention, substantial blood occlusion is considered to occur when an arterial pulsation signal measured at or distal to the pulse point is attenuated beyond a predefined threshold relative to a baseline value obtained at a lower, non-occlusive pressure.

According to some embodiments, the baseline arterial pulsation signal is measured when the pressure applicator is either not operated or is applied only at a low, non-occlusive pressure. This ensures that the baseline signal reflects arterial pulsations under conditions in which blood flow is substantially unimpaired.

According to some embodiments of the invention, such attenuation is indicative of substantial occlusion when the magnitude of the arterial pulsation signal (for example, a peak, peak-to-peak, or other amplitude measure) is reduced relative to a baseline value measured at a lower, non-occlusive pressure, for example by about 50% or more, by about 60% or more, or by about 70% or more.

According to some embodiments of the invention, substantial blood occlusion is considered to occur when an arterial pulsation signal measured at or distal to the pulse point falls below a predefined detection threshold and remains below that threshold for more than a predetermined number of consecutive cardiac cycles while the applied pressure is maintained. According to some embodiments of the invention, the predetermined number of consecutive cardiac cycles is, for example, at least 10, at least 20, at least 30, at least 40, at least 50, at least 60, at least 70, at least 80, at least 90, at least 100, at least 110, at least 120, at least 150, at least 200 cardiac cycles, optionally not exceeding. 5000, 4000, 3000, 1000, 500, e.g., 10-5000, 100-5000, 500-5000, 10-3000, 100-3000, 500-3000, 10-2000, 100-2000, 500-2000, 10-1000, 100-1000, 500-1000, 10-500, 50-500, 100-500, 200-500, 10-100, 50-100 cardiac cycles.

According to some embodiments of the invention, substantial blood occlusion is considered to occur when a parameter of local perfusion at or distal to the pulse point falls below a predetermined threshold indicative of compromised blood flow. According to some embodiments of the invention, the parameter of local perfusion comprises a photoplethysmography-derived parameter, a measure of tissue oxygenation, a measure of capillary refill time or a surrogate thereof, or another optical or physiological metric reflective of tissue perfusion. According to some embodiments of the invention, the predetermined perfusion threshold is selected such that values below the threshold correspond to a clinically or physiologically significant reduction in blood flow, as would be recognized by a person skilled in the art or user input.

According to some embodiments of the invention, the above-mentioned criteria are non-limiting examples and substantial blood occlusion may be identified when any one or more of these conditions are met, or when other objective or algorithmically derived indicators of materially reduced arterial flow are present, in accordance with the design and calibration of a particular implementation.

According to some embodiments of the invention, the pulse point is selected from one or more of a thumb, a finger, a wrist, an ankle and a temple. According to some embodiments, the device is selected according to the pulse point such as in terms of shape and size. According to some embodiments of the invention, the pulse point is located at or near the radial artery at the wrist, where the arterial pulse is commonly palpated in clinical examination. According to some embodiments of the invention, the pulse point is located at the palmar aspect of the thumb or finger, in proximity to digital arteries that provide a perceptible pulse. According to some embodiments of the invention, the pulse point is located above an artery at the ankle, such as the posterior tibial or *dorsalis* pedis artery, or at a temporal artery at the temple region of the head. According to some embodiments of the invention, the specific pulse point is selected based on user preference, accessibility, comfort, cosmetic considerations and/or the strength of the palpable pulse of the use. According to some embodiments, the mounting of the device may change based on the distance from the pulse point. For instance, when placed not on the pulse point a stronger pressure may be needed.

According to some embodiments of the invention, the controlled pressure level comprises at least about 5 mmHg at the skin surface over the pulse point.

According to some embodiments of the invention, the controlled pressure is in a range, for example from about 5 mmHg to about 60 mmHg, in some cases from about 5 mmHg to about 40 mmHg and in some cases from about 10 mmHg to about 25 mmHg.

According to some embodiments of the invention, the level of controlled pressure is maintained throughout a single session or multiple sessions of using the device. Maintaining the pressure level can be useful, for example, when the device is used to support sustained mindfulness practice. In other embodiments, maintaining the pressure level can be used to provide a stable tactile anchor during meditation, or to deliver a repeatable stimulus level for longitudinal biofeedback training across days or weeks.

According to some embodiments of the invention, the level of controlled pressure is varied during use of the device, for example according to a predefined temporal pattern and/or by intermittent (for example in a cyclical or heartbeat-synchronized pattern) or sporadic adjustments.

According to some embodiments of the invention, different variation patterns can be used for different relaxation or calibration purposes. For example, relatively slow, smooth oscillations in pressure can be used to gently draw the user's attention toward the pulse and maintain pulse awareness during a relaxation or mindfulness session. According to some embodiments, more pronounced and/or periodic increases and decreases in pressure can be used to cue paced breathing. Without being bound by theory such variations can encourage the user to inhale during one phase of the pressure cycle and exhale during another phase. According to some embodiments, intermittent pressure pulses can be used as alerts to re-engage the user's attention to the pulse rhythm when a loss of focus or mind wandering is detected or reported. In other implementations, heartbeat synchronized micro variations in pressure can be used to enhance perception of individual heartbeats and/or to facilitate cardiac training for stress reduction, anxiety relief and/or biofeedback assisted breathing exercises According to some embodiments of the invention, a "session" denotes a contiguous period of use of the wearable device during which the pressure applicator is activated to apply controlled pressure at a pulse point, e.g., without interruption in operation.

According to some embodiments of the invention, a single session begins when the device starts applying the controlled pressure according to a selected program or user command and ends when the application of controlled pressure is terminated, for example upon expiry of a preset duration, upon user command or upon automatic shut-off by a regulator.

According to some embodiments, a session begins when the user initiates operation of the device or selects a relaxation program and ending when the user terminates the program, removes the device, or the applied pressure is reduced below the desired range According to some embodiments of the invention, brief pauses or minor fluctuations that are inherent to the control algorithm or device operation, and that do not exceed a predetermined interruption interval (for example, not more than 5 seconds), do not terminate the single session.

According to some embodiments of the invention, the controlled pressure is maintained at or above about 5 mmHg for a time period exceeding about 20 second.

According to some embodiments of the invention, the controlled pressure is maintained for a time period in a range of about 1-60 minutes, e.g., 0.3-30, 0.3-25, 0.3-20, 0.3-15, 0.3-10, 0.3-5, 0.5-30, 0.5-25, 0.5-20, 0.5-15, 0.5-10, 0.5-5, 5-60, 10-60, 15-60, 20-60, 25-60, 30-60, 1-30, 2-30, 5-30, 10-30, 15-30, 2-20, 2-10, 1-30, 1-25, 1-20, 1-15, 1-10, 1-5, 5-60, 10-60, 15-60, 20-60, 25-60, 30-60, 1-30, 2-30, 5-30, 10-30, 15-30, 2-20, 2-10. According to some embodiments, the range is 5-10, 2-10, 2-7, 2-5, 0.5-5, 0.5-2, 0.5-3, 3-7, 3-10 minutes.

According to some embodiments, these ranges reflect different usability objectives.

In certain implementations, relatively short sessions of about 2-5 minutes are intended for rapid, on-the-go stress relief (for example, immediately before a meeting, public speaking event or other acutely stressful situation), where the user benefits from a brief period of enhanced pulse awareness without significant interruption to ongoing activities.

In other implementations, intermediate-length sessions of about 3-7 minutes are designed for focused mini-relaxation breaks during the day, providing sufficient time for the user to establish stable tactile perception of the pulse rhythm, engage in a brief breathing or mindfulness exercise and/or achieve a measurable relaxation response while still fitting within common break intervals.

In other implementations, longer sessions of e.g., 5-10 or 2-10 minutes or longer can be used for deeper relaxation or biofeedback-assisted breathing practice, such as pre-sleep wind-down routines or scheduled therapeutic use at home. These longer durations allow multiple respiratory cycles to be synchronized with the tactile pulse sensation and/or permit the autonomic nervous system to shift toward a parasympathetic-dominant state.

According to some embodiments of the invention, the level or rate of increase of controlled pressure is selected to avoid pain sensation during the application of pressure. According to some embodiments of the invention, the controlled pressure is adjusted in response to user feedback indicating discomfort or pain, such that the pressure is decreased or the session is paused when the user reports an unpleasant sensation. According to some embodiments of the invention, the method uses a predefined pain-avoidance protocol, in which the controlled pressure is initially set at a low level and gradually increased until the user reports a noticeable but comfortable sensation of heartbeat-related pulsation, while never reaching a level that induces pain. According to some embodiments of the invention, the non-painful pressure level determined during such a protocol is stored and subsequently used as a personalized operating level for future sessions. In other embodiments, the level or rate of increase of controlled pressure may cause pain.

According to some embodiments of the invention, the method comprises directing the user's attention to a tactile sensation at said pulse point corresponding or related at least in part to arterial pulsations associated with the user's self-heartbeats during application of said controlled pressure.

According to some embodiments of the invention, the user is advised, for example verbally, visually, or via an application interface, to focus attention on the sensation at the pulse point and to notice the rhythm and/or intensity of the perceived pulsations corresponding to their self-heartbeats. According to some embodiments of the invention, the directing of attention includes guiding the user through a brief protocol in which the user may alternate between focusing on external stimuli and refocusing on the tactile sensation, thereby training interoceptive awareness.

According to some embodiments of the invention, the directing of attention is facilitated by an audio signal that cues the user to attend to the tactile sensation at specific times, such as tones or spoken prompts synchronized with or alternating with the heartbeat sensations.

According to some embodiments of the invention, the audio signal comprises a heartbeat-like sound pattern (for example, a 'lub-dub' or 'boom-boom' sound) that is synchronized with, or representative of, the user's cardiac rhythm According to some embodiments of the invention, the directing of attention is facilitated by an optical signal presented to the user, for example by displaying a visual cue or animation that changes in synchrony with the user's heartbeat and/or with the application of the controlled pressure so as to visually represent the arterial pulsations.

According to some embodiments of the invention, the directing of attention is facilitated by a haptic signal presented to the user, for example by providing brief tactile cues at or near the time of the user's heartbeats so as to reinforce the association between arterial pulsations and perceived sensation.

According to some embodiments of the invention, the pressure applicator is operated directly by the user. According to some embodiments of the invention, the user initiates the pressure application by activating a user-operable element associated with the wearable device or with a device that communicates with the regulator, for example by pressing a button, tapping a touch surface, or selecting a start command through a software interface, thereby causing the regulator to begin applying the controlled pressure.

According to some embodiments of the invention, the user is able to manually increase or decrease the controlled pressure level during the session. According to some embodiments of the invention, the user can manually terminate the pressure application at any time.

According to some embodiments of the invention, the wearable device is operated automatically without user intervention. According to some embodiments of the invention, once the device is mounted and a session is initiated, a regulator associated with the device and/or an external computing apparatus automatically regulates the timing, amplitude and pattern of the controlled pressure according to a pre-programmed protocol and/or real-time feedback.

According to some embodiments of the invention, automatic operation includes closed-loop adjustments to the pressure based on monitored physiological signals or user-reported stress or pain, without requiring the user to manually adjust the device.

Figure 2:
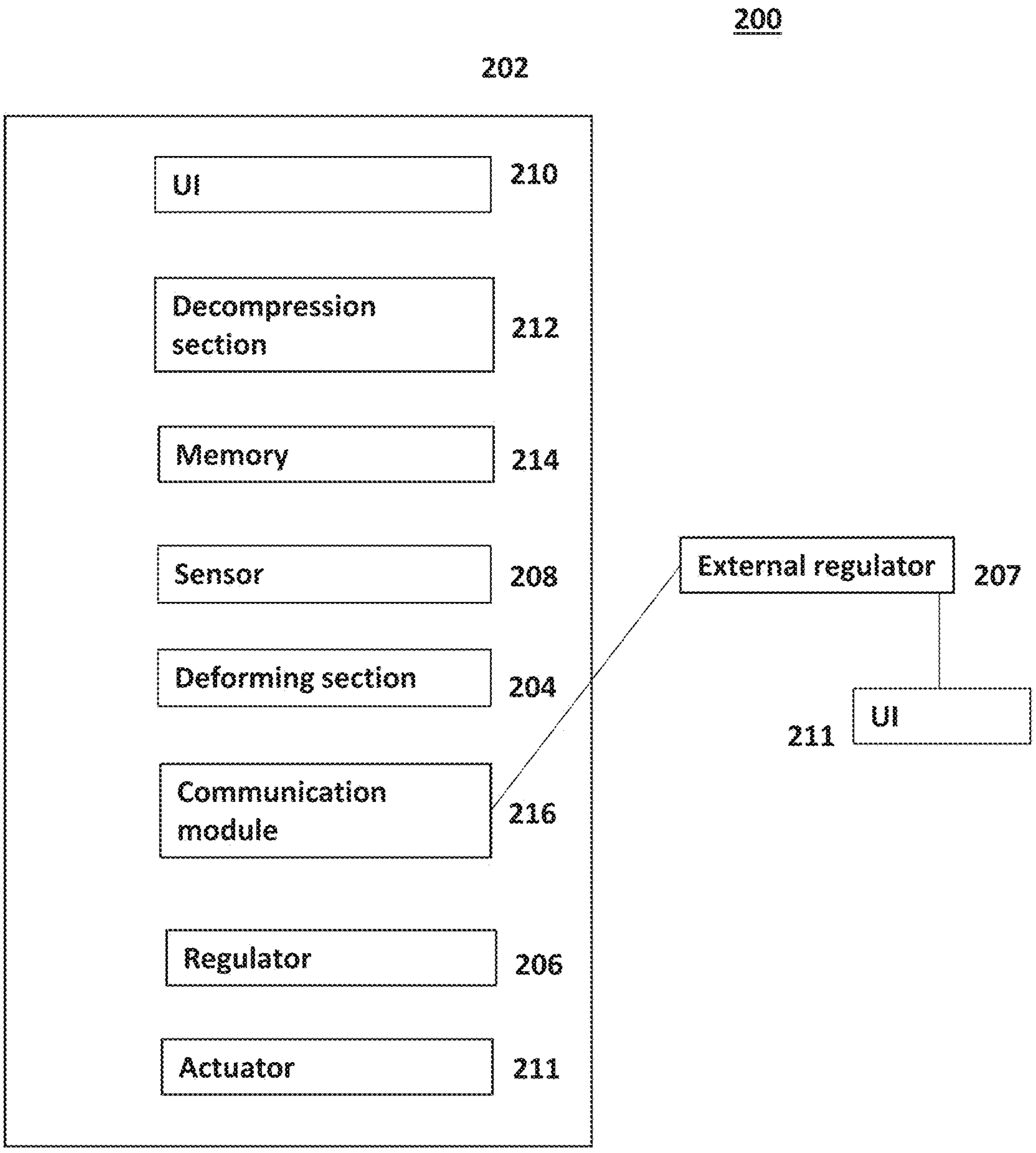
FIG. 2 is a box diagram describing a wearable device for increasing perception of self-heartbeats by a user, according to some embodiments of the invention.

A Device for Promoting Relaxation According to Some Embodiments of the Invention Embodiments of a device 200 for increasing perception of self-heartbeats by a user is described in FIG. 2.

According to some embodiments of the invention, the wearable device 200 comprises a body 202 sized and shaped for mounting against a pulse point of a user. According to some embodiments of the invention, the body 202 includes at least one integrated deforming section 204.

According to some embodiments of the invention, the device further comprises a regulator 206, which regulates the deforming section 204 to cause the body 202 to apply controlled pressure of at least 5 mmHg to a skin region comprising the pulse point and to maintain the controlled pressure or a variation thereof.

According to some embodiments, the deforming section 204 comprises an element integrated in (e.g., forming part of or attached to) the body 202 and configured, under control of the regulator, to undergo a change in shape, thickness and/or position relative to other parts of the body so as to modify mechanical loading on a skin region comprising the pulse point. The modification in mechanical loading may include directly pressing against said skin region, indirectly pressing said skin region by urging a non-deforming or designated contact section of the body 202 toward the pulse point (for example by acting on an opposite side of the finger or thumb), and/or stretching or tensioning skin over or adjacent to the pulse point, thereby applying, maintaining and/or varying the controlled pressure.

According to some embodiments, the deforming section 204 comprises at least one actuator selected from the group consisting of a pneumatic chamber, a hydraulic chamber and a shape memory alloy actuator, which when actuated causes the integrated deforming section 204 of the body 202 to deform toward or away from the skin region comprising the pulse point.

In some embodiments, when actuated, the deforming section 204 locally changes a contour, thickness and/or position of at least a part of body 202 relative to its initial, undeformed state so as to increase or decrease the pressure applied by body 202 to the skin region comprising the pulse point. In this manner, the deformation of body 202 at the location of deforming section 204 produces the controlled pressure.

According to some embodiments, when the actuator of deforming section 204 is implemented as a pneumatic chamber, the pneumatic chamber is in fluid communication with a pump and/or a controllable valve controlled by regulator 206. In such embodiments, inflation of the pneumatic chamber (e.g., by introducing air or another gas from a reservoir connected to the pneumatic chamber) locally increases the thickness and/or outward protrusion of the deforming section 204 relative to the inner circumference of body 202, thereby driving a skin-contact region of the body 202 toward the skin region comprising the pulse point and increasing the pressure applied to that region. Deflation of the pneumatic chamber conversely reduces the thickness or protrusion of deforming section 204 and decreases the applied pressure, or removes it altogether. The geometry, wall compliance and/or maximum inflation volume of the pneumatic chamber can be selected such that the controlled pressure at the skin can be set and maintained as necessary.

According to some embodiments, when the actuator of deforming section 204 is a hydraulic chamber, the hydraulic chamber is filled with a liquid, such as water, saline, silicone oil or other biocompatible fluid. According to some embodiments, the hydraulic chamber is coupled to a micro-pump and/or electronically controllable valve. In some embodiments, addition of fluid into the hydraulic chamber increases internal volume and outward deformation of deforming section 204, thereby increasing pressure at the pulse point. According to some embodiments, removal of fluid causes the deforming section 204 to retract and reduces the pressure. According to some embodiments, the use of an incompressible fluid allows fine control of displacement and, correspondingly, of the applied pressure, as regulated by regulator 206. According to some embodiments, the regulation can be based on sensor data.

According to some embodiments, when the actuator of deforming section 204 comprises a shape memory alloy (SMA) actuator, the SMA element (for example, a wire, strip or spring) is embedded within or mechanically coupled to the material of body 202 in the region of deforming section 204. In such embodiments, upon application of an electrical current or other heating stimulus under control of regulator 206, the SMA element undergoes a phase transformation and changes length and/or curvature. This controlled dimensional change produces a bending, bowing and/or protruding deformation of deforming section 204 toward the skin region comprising the pulse point, thereby applying the controlled pressure. According to some embodiments, when the stimulus is reduced or removed, the SMA element returns toward its original state and the deforming section 204 correspondingly moves away from the skin, reducing the applied pressure. The SMA-based deforming section is optionally configured to provide quasi-static pressure levels, time-varying pressure patterns, or both.

According to some embodiments, the deforming section 204 may include a combination of two or more of the above actuators, for example a pneumatic chamber pre-biased or shaped by an SMA element, thereby enabling different operating modes (e.g., coarse positioning and fine modulation of pressure). According to some embodiments, the actuators of deforming section 204 are mechanically and/or adhesively integrated within the structure of body 202 such that actuation results in a localized deformation of body 202 at a region that is aligned with the pulse point when the device is properly mounted. This integrated configuration preserves the overall form factor of the wearable (e.g., thumb or finger cover e.g., full cover or a clipper, wristband or patch) while providing a controllable, repeatable deformation against the user's skin.

In some embodiments, the regulator 206 sends control commands (with or without feedback, e.g., open-loop or closed-loop actuation, respectively) to the actuator(s) in deforming section 204 so that the resulting shape change of the body 202 creates a desired and controlled pattern of pressure over time at the user's pulse point.

In some embodiments, regulator 206 receives data from one or more sensors.

According to some embodiments, regulator 206 is also referred to as a "controller". According to some embodiments, a regulator denotes control circuitry configured to generate one or more control signals for driving the actuator (s) of the deforming section 204. The regulator 206 may include, for example, one or more processors, microcontrollers, digital signal processors (DSPs), application-specific integrated circuits (ASICs), field-programmable gate arrays (FPGAs), memory devices storing executable instructions, and associated analog and/or digital interface circuitry, power management circuitry and communication interfaces.

In some embodiments, regulator 206 is physically integrated in the wearable device (e.g., within body 202) and is configured to locally control the actuator(s) of deforming section 204. In other embodiments, at least a portion of the regulator (or all regulating functions) is external to the wearable device and may referred to as an external regulator 207. For example, the regulator 207 may be implemented in an external device such as a smartphone, smartwatch, tablet, computer, base station or cloud server that communicates with the wearable device via a wired or wireless communication module 216 (e.g., Bluetooth, Wi-Fi, NFC or other protocol). In such embodiments, the external controller may generate all or part of the control signals and transmit corresponding commands to the regulator 206 which in such a case may be a simpler driver circuit within the body 202, which in turn energizes the actuator(s) of deforming section 204. In some embodiments, the external regulator 207 is configured to communicate with known or conventional wearable device such as a blood-pressure meter with an inflatable cuff, vascular occlusion device or other pressure-applying apparatus or other compression device such as a therapeutic device. In such an embodiment, initiation of operation of the external regulator 207 can itself be used as an intervention to promote relaxation, according to some embodiments of the invention. Upon activation, the external regulator 207 causes the known medical device to implement a pressure-application protocol (such as greater than about 5 mmHg) for a duration exceeding a predetermined minimum time (such as more than about 20 seconds), thereby enhancing bodily awareness to self-heartbeats and facilitating a relaxed physiological state.

In some embodiments, a portion of the regulator functionality is provided by regulator 206 which is located within the wearable device 200 and another portion is provided by an external regulator 207. For instance, the external regulator 207 may execute higher-level algorithms (e.g., determining a target pressure profile at the pulse point) and the local regulator 206 may perform lower-level closed-loop actuation control such as based on local sensor feedback.

According to some embodiments of the invention, the device further comprises at least one sensor 208, which can be also be referred to as a sensing module or a sensing circuitry.

According to some embodiments of the invention, the sensor 208 is a safety sensor that is configured to detect an effect of the wearable device on the user's body.

According to some embodiments of the invention, the safety sensor is configured to directly or indirectly sense one or more physiological or tissue-level responses to operation of the wearable device. Examples include, but are not limited to, changes in blood flow, perfusion, or vascular occlusion in a tissue underlying the device; changes in optical signals such as PPG amplitude, waveform shape, or baseline associated with altered hemodynamics caused by device-applied pressure; changes in tissue displacement, indentation depth, or tissue stiffness/compliance under the applied pressure; skin condition parameters such as color, blanching, erythema, temperature, moisture, or other indicators of irritation or ischemia; and/or user motion or postural changes that, in combination with the applied pressure, may lead to an unsafe or undesirable condition.

According to some embodiments of the invention, the safety sensor comprises one or more optical sensors (for example, PPG sensors), contact pressure or force sensors, strain or deformation sensors arranged to infer tissue response, temperature sensors, bioimpedance sensors, or other biosensors capable of measuring a parameter indicative of how the user's tissue is responding to the applied pressure. According to some embodiments of the invention, signals from the safety sensor are provided to the regulator 206 or 207, which is configured to determine, based on the sensed effect of the wearable device 200 on the body, whether one or more safety criteria or thresholds are met and, in response, to adjust, limit, or terminate actuation and/or to place the device in a safe state.

According to some embodiments of the invention, the at least one sensor 208 comprises a physiological sensor. According to some embodiments of the invention, the physiological sensor is configured to detect one or more physiological parameters that are indicative of a stress level of the user and to provide corresponding physiological data to the regulator. According to some embodiments of the invention, the physiological sensor detects a physiological signal selected from the group consisting of heartbeat, respiration, heart rate variability, blood pressure and blood pressure variability. According to some embodiments, the regulator is configured to adjust the controlled pressure and/or other operating parameters of the device based on the detected physiological signal and/or the physiological data derived therefrom. According to some embodiments, the regulator uses the detected physiological signal and/or derived data to assess user stress and/or track the relationship between device usage and stress over time without directly controlling the applied pressure in real time.

According to some embodiments of the invention, when the physiological data indicate that the user is in a first, lower-stress state (for example, normal heart rate, normal heart rate variability and/or relatively stable blood pressure), the regulator controls the deforming section to apply a first pressure profile at the pulse point, for example a relatively lower average pressure and/or a slower modulation pattern. According to some embodiments of the invention, when the physiological data indicate that the user has transitioned to a second, higher-stress state (for example, elevated heart rate and/or respiration rate, reduced heart rate variability and/or increased blood pressure variability), the regulator automatically adjusts the controlled pressure, for example by increasing a magnitude, duty cycle and/or frequency of the pressure modulation at the pulse point, in order to apply a pressure profile that is predefined for stress-reduction or autonomic modulation. According to some embodiments of the invention, when the physiological data indicate that the user's stress-related parameters have returned toward a baseline range, the regulator 206 correspondingly reduces or terminates operation of the deforming section, or returns the pressure to a standby level suitable for monitoring only.

According to some embodiments of the invention, the at least one sensor 208 comprises a device operability sensor. According to some embodiments, the device operability sensor generates a signal indicating proper mounting of the body at a skin region comprising the pulse point.

According to some embodiments of the invention, the operability sensor is configured to detect whether the device is in a condition suitable for performing stress-related sensing and/or pressure application and to provide corresponding operability data to the regulator. The operability sensor may comprise, for example, a pressure sensor configured to detect a contact pressure between the device and the user's skin, an acceleration or motion sensor configured to detect movement of the device relative to the user's body, a PPG or other optical sensor configured to detect whether a stable physiological signal (such as heartbeat, respiration or heart rate variability) is present at the intended measurement site, and/or a touch or capacitive sensor configured to detect that the device is correctly worn. When the operability sensor indicates that the contact pressure is within a desired range and that a reliable physiological signal is detected, the regulator may enable or optimize operation of the deforming section and adjust the controlled pressure based on the physiological data and/or physiological signal received from the physiological sensor (for example, heartbeat, respiration, heart rate variability, blood pressure or blood pressure variability that are indicative of the user's stress level). Conversely, when the operability sensor detects that the device is not properly mounted, that the contact pressure is too low or too high, or that the physiological signal quality is insufficient, the regulator may inhibit, reduce or modify the operation of the deforming section until proper operability is restored. Alternatively or additionally, the regulator informs the user from UI to re-position the device.

According to some embodiments of the invention, the components of the device such as the sensors and the deforming section can be moved easily for better mounting of the device; for example, the pressure sensor, the physiological sensor and/or the deforming section may be mounted on a movable or rotatable carrier that allows repositioning along the inner circumference of a ring or along a strap, so that the user can manually adjust, or the system can guide the user to adjust, these components to an anatomical location at which the operability sensor confirms adequate contact and a stable stress-related physiological signal.

According to some embodiments of the invention, the components of the device such as the sensors and/or the deforming section can be moved easily for better mounting of the device; for example, the pressure sensor, the physiological sensor and/or the deforming section may be mounted on a movable or rotatable carrier that allows repositioning along the inner circumference of a ring or along a strap, so that the user can manually adjust. According to other embodiments, the system can guide the user to adjust, these components to an anatomical location at which the operability sensor confirms adequate contact and a stable stress-related physiological signal.

In some embodiments, the movable or rotatable carrier comprises a mechanically guided element such as a slidable track, rail, or groove, a circumferential channel, and/or a hinge- or pivot-mounted sub-frame, optionally biased or lockable by a detent, spring, friction fit, or clasp, thereby structurally enabling repeatable repositioning and secure fixation of the sensors and/or deforming section at different locations along the ring or strap According to some embodiments of the invention, the device comprises a user interface (UI) 210. According to some embodiments, the UI 210 can be part of body 202 or external thereto as in UI 211. Each of UI 210, 211 can be for receiving external information from the user. According to some embodiments of the invention, the external information is selected from the group consisting of stress level, preference for duration of the controlled pressure appliance and environmental conditions. According to some embodiments, the external information can be turn on turn off. According to some embodiments of the invention, the user interface comprises a control element for pressure adjustment by the user. According to some embodiments of the invention, the user interface includes one or more buttons, touch elements, graphical interface elements, and/or communication interfaces for receiving the external information and/or for enabling the user to increase or decrease the controlled pressure within an allowed range.

According to some embodiments of the invention, the device further comprises an actuator 211 that generates a human perceptual signal corresponding to the self-heartbeats. According to some embodiments of the invention, the human perceptual signal is selected from the group consisting of an acoustic signal, a haptic signal, an optical signal and a combination of two or more of these signals. According to some embodiments of the invention, the human perceptual signal is synchronized with, derived from and/or corresponds to the user's self-heartbeats. According to some embodiments the human perceptual signal is presented to the user to enhance perception of the self-heartbeats and to direct attention to the interoceptive experience.

According to some embodiments of the invention, the body 202 comprises a decompression section 212, which physically changes to apply pressure. According to some embodiments, the decompression section 212 comprises a circuitry controlled by the regulator 206 in response to the regulator receiving a signal from the sensor 208 and/or from the user. According to some embodiments of the invention, the decompression circuitry comprises a mechanical circuitry, for example a valve, vent, relief mechanism or mechanical linkage configured to reduce the controlled pressure when actuated by the regulator. According to some embodiments of the invention, the decompression section 208 is an electronic circuitry, for example a driver of an electronically controlled valve, pump driver, or actuator driver that decreases the pressure in accordance with control signals provided by the regulator.

According to some embodiments of the invention, the regulator comprises is configured to selectably operate in a calibration mode configured for determining a personalized range of the controlled pressure based on at least one of user preferences and a safety parameter comprising blood flow. According to some embodiments of the invention, the user preference is based on pain threshold of the user. According to some embodiments of the invention, the user preference is based on pleasure feeling of the user in response to the pressure. According to some embodiments of the invention, during the calibration mode the regulator 206 controls the deforming section to vary the pressure while receiving user input via the user interface and/or safety data via the safety sensor, and determines a personalized range of pressures that satisfy desired perception, comfort and blood flow criteria. When the regulator is external, as in 207 it can control the deforming section. According to some embodiments of the invention, this personalized range is stored and subsequently used by the regulator during operation.

According to some embodiments of the invention, the regulator 206 is configured to vary the controlled pressure over time. According to some embodiments of the invention, varying the pressure over time comprises modulating pattern e.g., amplitude and/or duration of the applied pressure within the personalized range or within a range. Such as at least 5 mmHg and is maintained for a time period exceeding 20 seconds. According to some embodiments of the invention, varying the pressure over time enhances the transfer of arterial pulsations and maintains or increases perception of the self-heartbeats.

According to some embodiments of the invention, the device comprises at least one memory operatively coupled to the regulator. The memory is configured to store data and/or instructions used for operation of the deforming section and for personalization to the user. The stored information may include, for example, one or more pressure protocols defining temporal profiles of the controlled pressure (such as magnitude, rise and fall times, duty cycle, frequency and duration of pressure application), as well as or instead user-specific data such as baseline physiological values, stress-related thresholds, user identification data, historical physiological measurements and/or historical pressure-application records. The memory may additionally store operating parameters, calibration data and/or software or firmware instructions executable by the regulator to implement stress-detection and pressure-control algorithms. The regulator is configured to read from and/or write to the memory, for example to select a pressure protocol in response to current physiological data received from the physiological sensor, to update stored user-specific thresholds based on long-term trends, and to log physiological data and applied pressure patterns for later analysis or for transfer to an external device.

In some embodiments, the memory is non-volatile memory integrated within the smart ring. According to some embodiments, the regulator (which may correspond to, or be implemented by, the operation processor shown in FIG. 4A-D) accesses the memory via one or more internal communication buses. According to some embodiments, the pressure-control of the device can be adapted dynamically according to the stored protocols and user data.

Figure 3A:
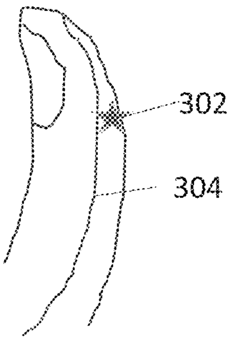
Figure 3B:
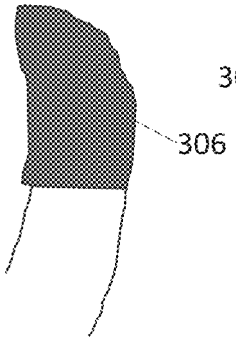
Figure 3C:
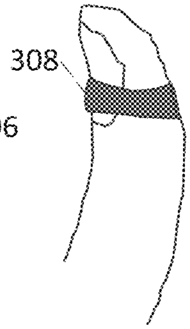
Figure 3D:
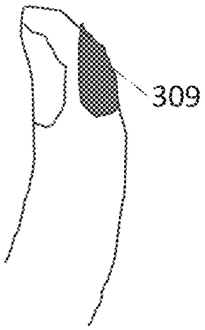
Figure 3E:
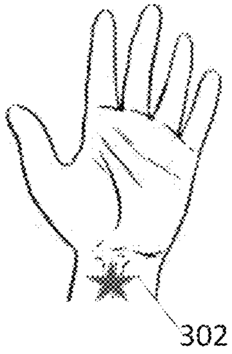
Figure 3F:
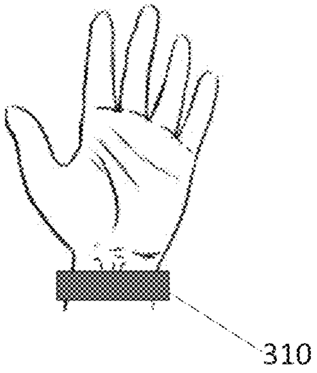

According to some embodiments of the invention, the wearable device 200 is selected from the group consisting of a thumb or finger cover, a wristband and a patch configured for positioning over a pulse point of the user. It will be appreciated that any of the ring or bands need not completely Some possible exemplary configurations of such a device are shown in FIGS. 3A-F. Pulse points on thumbs and wrists are shown as a stars in FIGS. 3A and 3E. According to some embodiments of the invention, the body 306 is shaped as a cover in FIG. 3B or a ring 308 in FIG. 3C. According to some embodiments of the invention, the body is shaped as a wristband 310 in FIG. 3F that encircles at least part of the wrist and positions the deforming section over a radial or ulnar pulse point. According to some embodiments of the invention, the body 309 of FIG. 3D is shaped as a patch that adheres or is otherwise affixed over a pulse point. It will be appreciated that any of the wearables, e.g., rings or bands, need not completely encircle the relevant body part. According to some embodiments, the wearable may be a partially circumferential structure. Examples include but are not limited to a C-shaped, U-shaped, split, hinged, or otherwise partially circumferential structure. Such a structure, in some embodiments, is configured to resiliently grip, clamp onto or otherwise maintain stable contact with the target pulse area while still permitting donning, removal, and adjustment by the user. In some embodiments, a partially circumferential structure can comprise one or more elastic, flexible, or spring-biased portions (for example, formed of elastomers, shape-retaining polymers, spring metals, or embedded spring elements) that allow the opening to elastically widen for placement over the finger or thumb. In some embodiments, it may then contract to a smaller optionally comfortable diameter such as to provide secure, conformal contact during use.

According to some embodiments of the invention, the pulse point is a thumb, a finger, a wrist, an ankle and/or a temple. According to some embodiments of the invention, the body 202 and deforming section 204 are shaped and/or sized to conform to the local anatomy of the selected pulse point and to apply the controlled pressure to the skin region comprising the pulse point to augment transfer of arterial pulsations corresponding to the user's self-heartbeats to a sensing nerve of the user.

According to some embodiments of the invention, the device further comprises a power source for operating at least one of the regulator 206 and the deforming section 204 and/or other components of the device. According to some embodiments of the invention, the power source is integrated within the body, for example as a rechargeable battery, or is external and operatively connected to the regulator and/or the deforming section.

Exemplary Wearables According to Some Embodiments of the Invention

Reference is now made to FIGS. 4A-D that provide some illustrative examples of wearable 400 (which can be an example of wearable 200 of FIG. 2), for example a ring or a band, having body 402 (similar to body 202 of FIG. 2) and a deforming section 404 (similar to deforming section 204 of FIG. 2) integrated therein. For example, the device of FIGS. 4A-B comprises body 402, at least one deforming section 404 (FIG. 4A) or more (FIG. 4B), which is integrated within and spans at least a portion of an inner circumference of body 404. Deforming section 404 can be filled with a flowable substance e.g., a liquid, gel or gas.

Figure 4A:
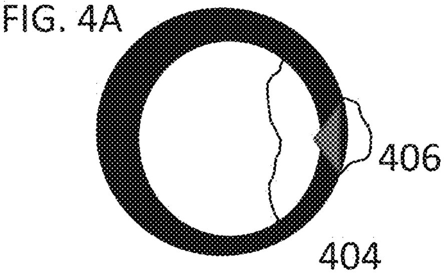
Figure 4B:
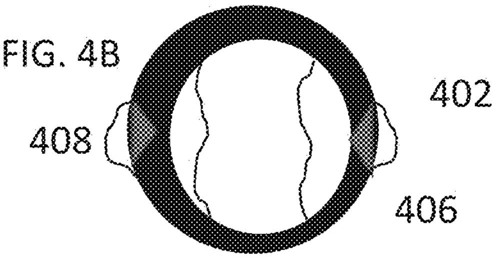
Figure 4C:
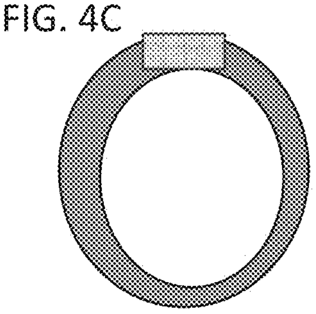
Figure 4D:
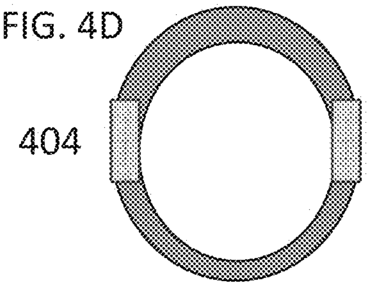

Deforming sections 404 can be opposite each other with respect to the inner circumference of the wearable 400, e.g., band or ring, as shown in FIGS. 4B and 4D.

The device of FIGS. 4A-B optionally comprises at least one pump 406, which pumps flowable substance from an outer elastic member 408 into the deforming section 404, or vice versa. Pumping can be done automatically and/or by the user.

Another example is illustrated in FIGS. 4C-4D, in which one or more deforming section(s) 404 are integrated into body 402 and are formed from a shape-memory alloy. Body 402 may include one or more inelastic portions or segments (e.g., rigid and/or substantially inflexible segments) and one or more elastic portions or segments (e.g., stretchable, articulated, and/or flexible segments). This segmented configuration allows the wearable device to conform to the user's anatomy while applying a controlled pressure at one or more pulse points.

FIG. 5A-B are schematic illustrations of an exemplary wearable devices shaped as a ring 500. Ring 500 comprises body 502 (which is similar to body 202 of FIG. 2), and deforming section 504 (which is similar to deforming section 204 of FIG. 2), regulator 606 and various types of sensors e.g., at least one of 508, 510 and 512 which represent operability sensor, safety sensor and a physiological sensor described above with respect to FIG. 2. FIG. 5B shows the application of ring 500 on a finger of user's hand 520.

Computer-Executable Instructions for Determining a Pressure Variation and Wirelessly Controlling a Pressure-Applying Device According to Some Embodiments of the Invention Reference is now made to FIG. 6, which is a flow diagram describing a software that controls how pressure is applied at the user's pulse point. In some these software instructions are stored on a non-transitory computer-readable medium. The instructions are executable by at least one processor and, when executed, cause the at least one processor to communicate with a device that is configured to apply pressure to a pulse point of a user as shown in block 602, determine a variation in pressure to be applied by the device in block 604, convert the determined variation in pressure into control commands for the device in block 606, and wirelessly transmit the control commands to the device in block 608 in order to control operation thereof. According to some embodiments, the non-transitory computer-readable medium is comprised in a mobile communication device, and the instructions corresponding to blocks 604, 606 and/or 608 form part of a downloadable application installed on said mobile communication device.

According to some embodiments, the device configured to apply pressure to the pulse point may be implemented as the wearable device 200 described herein in FIG. 2.

According to some embodiments, to "communicate with" the device as shown in block 602, the at least one processor may establish a wired or wireless communication link with the device, such as via Bluetooth®, Wi-Fi, a cellular network, or another suitable short-range or long-range wireless protocol.

In one embodiment, the wearable device includes a wireless communication interface or transceiver operatively coupled to the regulator (such as regulator 206 of FIG. 2) and the at least one processor transmits and receives data packets over such wireless interface. The regulator is operatively coupled to the deforming section and, based on pressure-control commands received from the at least one processor, controls the deforming section to apply, maintain, and/or vary the controlled pressure at the skin region comprising the pulse point According to some embodiments, communication between the wearable device and an external device includes exchanging identification information and/or configuration data during setup, and transmitting sensor readings and receiving pressure-control commands during operation.

In some embodiments, the instructions cause the processor to determine a variation in pressure to be applied by the device based on one or more inputs, as shown in block 604. According to some embodiments, the variation in pressure comprises a temporal profile of pressure values generated from the one or more inputs, for example from stored configuration data, real-time sensor readings, and/or control parameters received from an external device, such as a sequence of target pressure levels, a modulation pattern, or a pressure waveform synchronized with a physiological signal of the user. The determination may be performed based on one or more of: user-specific calibration data; real-time physiological measurements (e.g., PPG waveforms, heart rate, or arterial pulsation characteristics); user-selected programs (e.g., relaxation, focus, alertness); or historical usage and response data.

In certain embodiments, the determination of the variation in pressure includes using calibration data obtained during a prior calibration procedure in which a level of pressure sufficient for the user to perceive self-heartbeats, optionally without causing substantial blood occlusion at the pulse point, has been established. According to some embodiments, the calibration information and pressure-profile parameters are stored and/or generated at least in part by a companion relaxation or biofeedback application executing on a smartphone or other external device, or by an associated cloud-based relaxation service, and are communicated to the wearable device. In other embodiments, such calibration information is stored directly on the wearable device. In any of these cases, the instructions cause the processor to access the calibration information and to generate a variation in pressure that oscillates about, or otherwise references, the calibrated non-occlusive level so as to enhance perception of self-heartbeats and/or promote relaxation of the user.

According to some embodiments, once the variation in pressure has been determined, the instructions further cause the processor to convert the determined variation into control commands for the device, as shown in block 606. The control commands may specify, for example, absolute pressure setpoints, incremental pressure changes, actuator drive levels, timing information, or other parameters usable by the device to realize the desired pressure pattern. In some implementations, the processor may translate high-level desired pressure values into lower-level hardware-specific commands, such as duty-cycle values, pump drive signals, motor position commands, valve-open durations, or the like.

According to some embodiments, the processor then wirelessly transmits the control commands to the device so as to control operation thereof. Wireless transmission may be performed periodically or continuously, in accordance with the determined variation in pressure, and may be updated in real time in response to changes in physiological state or user input. In some embodiments, the processor also receives acknowledgement messages and/or sensor feedback from the device, and may adjust subsequent control commands based on the received feedback, thereby implementing a closed-loop pressure-control process.

In some embodiments, the at least one processor that executes at least some of the above-described instructions is comprised in a mobile communication device. For example, the mobile communication device may be a smartphone, tablet computer, smartwatch or other portable electronic device carried by the user. The mobile communication device may include a wireless communication module configured to pair with the pressure-applying device, a user interface allowing the user to start and stop pressure-control sessions or select among different pressure-variation programs, and a data storage component for storing calibration information, physiological data, and historical usage records. In such embodiments, the mobile communication device acts as an external controller that remotely drives the pressure-applying device according to the instructions stored on the non-transitory computer-readable medium.

In other embodiments, the at least one processor is comprised in a remote server configured to communicate with the device via a network. For example, the remote server may be part of a cloud-based system that receives usage data and/or physiological measurement data from the device and/or from a mobile communication device associated with the user, determines or updates one or more pressure-variation programs based on such data, and transmits corresponding control commands to the device via a wide-area network.

According to some embodiments, the remote server hosts algorithms, for example machine learning models, that process historical and real time user data such as heart rate variability, respiration patterns, usage history, and user feedback entered through a relaxation or biofeedback application, in order to identify pressure variation patterns associated with desired outcomes including enhanced pulse awareness or perceived relaxation. Based on this analysis, the remote server generates or updates individualized pressure variation profiles, including values for pressure amplitude, timing, and synchronization with physiological signals, and provides corresponding updated instructions or control parameters that are downloaded to the wearable device or to an intermediate mobile communication device executing the relaxation software.

In yet other embodiments, the overall system may employ a combination of a mobile communication device and a remote server. For instance, the mobile communication device may execute locally stored communication and control instructions, including instructions for acquiring sensor data from the wearable device, applying user interface inputs to select or modify relaxation programs, and issuing real time pressure control commands to the wearable device. The remote server may execute data analysis and personalization instructions, including algorithms that derive or update configuration parameters, calibration values and/or pressure variation templates based on aggregated data across multiple sessions or users and may periodically provide updated parameters or templates to the mobile communication device and the wearable device.

In all such arrangements, the non-transitory computer-readable medium may be located locally on the mobile communication device, on the remote server, on the pressure-applying device itself, or distributed among these components, and the instructions stored thereon are configured, when executed, to implement the communication, determination, conversion and transmission operations described above.

By way of non-limiting example, in one embodiment the non-transitory computer-readable medium is comprised in a smartphone of the user and stores an application that, when executed by one or more processors of the smartphone, performs: (i) communicating with the pressure-applying wearable device (corresponding to block 602), (ii) determining a variation in pressure to be applied by the device (block 604), (iii) converting the determined variation in pressure into control commands (block 606), and (iv) wirelessly transmitting the control commands to the device (block 608). In this embodiment, the wearable device itself may additionally comprise a local non-transitory memory storing instructions executed by an embedded microcontroller to implement low-level actuation of a deforming section in response to the received control commands.

In some embodiments, the pressure applied by the wearable device to the pulse point of the user is controlled, at least in part, by an external computing device, such as a smartphone, tablet computer, laptop computer, desktop computer, or remote server. The external computing device may comprise at least one processor, a memory storing instructions executable by the at least one processor and a wireless communication module configured to communicate with the wearable device. During operation, the at least one processor may communicate with the wearable device via the wireless communication module, determine a variation in pressure to be applied by the wearable device, convert the determined variation into control commands and wirelessly transmit the control commands to the wearable device to control operation of the wearable device.

In some implementations, the control commands received by the wearable device are provided to the regulator, which in turn controls the deforming section to implement the determined variation in pressure at the pulse point.

Calibrating a Device for Increasing Perception of Self-Heartbeats by a User According to Some Embodiments of the Invention According to some embodiments of the invention, mounting of the device and parameters of operation are calibrated such as to determine a personalized effective pressure level which may be affected by anatomical and physiological parameters. The calibrated level (or range) may be stored and reused automatically in subsequent sessions.

Reference is made to FIG. 7 in which a calibration process of the wearable device is disclosed according to some embodiments of the invention.

Mounting the wearable device against a pulse point of the user and applying pressure at the pulse point to augment transfer of arterial pulsations corresponding to self-heartbeats from an artery to a sensing nerve of the user are referred to in blocks 702 and 704 and may be, for example, as described above with reference to FIG. 1, blocks 102 and 104, respectively.

Embodiments of determining a level of pressure sufficient for the user to perceive self-heartbeats are described in block 706.

According to some embodiments of the invention, determining a suitable level of pressure comprises gradually increasing the applied pressure from an initial low value while the user is to concentrate on whether self-heartbeats are felt at the pulse point and report whether and to what extent the self-heartbeats are perceived. According to some embodiments of the invention, the applied pressure is increased in small increments, for example by user activation of a control element associated with a regulator, by automatic operation of the regulator, or by a clinician or technician supervising the calibration procedure. According to some embodiments, the gradual increase may be implemented as a continuous ramp-up of pressure or as a sequence of discrete pressure steps separated by short rest intervals (for example, intervals on the order of a few seconds), starting from a low baseline pressure that is below a typical pulse perception threshold and continuing until a user-reported or pre-defined perception criterion is met, thereby empirically identifying a user-specific therapeutic pressure range.

According to some embodiments of the invention, at each increment the user provides an indication of heartbeat perception, for example by verbal report, by activation of a user input element and/or by selection of a value on a scale presented via a software interface. According to some embodiments of the invention, the calibration procedure continues until a threshold of perception is reached, for example a first pressure level at which the user consistently reports clear perception of self-heartbeats at the pulse point.

According to some embodiments of the invention, during the calibration procedure the condition of "no substantial blood occlusion" is verified by ensuring that arterial blood flow at or distal to the pulse point remains adequate, for example by palpation, by measurement of pulse waveform or peripheral perfusion or by confirming absence of symptoms such as numbness, pain, or discoloration. According to some embodiments of the invention, if indications of substantial blood occlusion are detected, the applied pressure is reduced and the threshold determination is repeated at lower pressure levels.

According to some embodiments of the invention, the determined level of pressure corresponds to a range or window of acceptable pressures rather than a single value, for example a range bounded by a lower limit at which perception of self-heartbeats begins (also referred to as effective pressure) and an upper limit below which substantial adverse effects such as blood occlusion and/or pain do not occur.

According to some embodiments of the invention, the calibrated level of pressure, or a value derived therefrom, is stored, for example in an electronic memory associated with the regulator, with the wearable device, or with an external computing apparatus, and is subsequently used as a target pressure level in a method of increasing relaxation of the user.

According to some embodiments of the invention, the calibration procedure is repeated periodically, for example at different times of day or under different physiological or environmental conditions, in order to update the pressure level used in subsequent relaxation sessions. According to some embodiments of the invention, multiple calibrated pressure levels are determined for different body positions, pulse points, or user states (e.g., resting, mildly stressed) and a particular calibrated level is selected for use in a relaxation method based on current conditions or user preference.

The range of acceptable pressures gleaned from the calibration steps can be used in a method of promoting relaxation of the user as referred to in block 708. Such a method is described hereinunder.

A Method of Promoting Relaxation According to Some Embodiments of the Invention

In some embodiments, the present invention provides a method for promoting relaxation or reducing stress in a user by applying controlled pressure at a skin region comprising a pulse point. Embodiments of the method are described in FIG. 8.

According to some embodiments, the user may be an adult, adolescent or a child from any gender experiencing acute stress, anxiety or difficulty relaxing. For example during a demanding workday, following an emotionally challenging event, in anticipation of a stressful encounter, or when attempting to transition to sleep. In other scenarios, the user may engage the method before or after a test or examination (e.g., school exam, professional certification), before or after a job interview, before, during or after a medical examination (for example, a dental procedure), or in connection with social anxiety or social phobia, such as prior to or following a socially challenging interaction or event. In other scenarios, the user may have a baseline of chronic stress or a desire to incorporate short relaxation sessions into an ongoing wellness or self-care routine. The method can be practiced in a variety of settings, including at home, at work, in a clinical or therapeutic environment, while traveling or in other daily-life contexts or it may be triggered automatically, based on sensing or pre-determined schedule.

According to some embodiments, the method involves positioning a device which comprises a pressure applicator at a pulse point of the user. In some embodiments, the device is the wearable device 200 of FIG. 2, for example, configured as a wristband or bracelet adapted to be worn around the wrist, such that the pressure applicator is alignable with the radial artery. In other embodiments, the device is configured to be worn or placed at the thumb, a finger, the ankle (e.g., over the posterior tibial or *dorsalis* pedis artery) or at the temple region of the head. These can be further decorated such as with a watch, a gem, an inscription, a drawing or any other decoration. The user may position the device manually, tightening or adjusting a strap or band to secure the pressure applicator over or in the vicinity the desired pulse point. In other embodiments, the device is automatically operated for example, the wearable device 200 may include a motorized or otherwise actuated deforming section that automatically adjusts its position or tightness based on feedback from a sensor configured to detect arterial pulsations, or based on pre-programmed placement instructions.

In some embodiments, the device is automatically operated, for example, when a triggering condition is satisfied such as detection of a stress-related physiological pattern, expiry of a scheduled reminder time, receipt of a user-defined start command via a companion app, or detection that the device has been correctly positioned at a pulse point, and in such cases the automated operation may be used not only to initiate or conduct a relaxation or treatment session but also to perform non-therapeutic functions such as calibration, signal-quality optimization, data logging, or demonstration modes.

In some embodiments, the pressure applicator is operated directly by the user (e.g., by pressing a mechanical button, sliding a mechanical control, or using a smartphone app to increase or decrease pressure); in other embodiments, the device is automatically operated by an on-board controller or an external computing device executing a relaxation protocol with minimal required user interaction.

When the device is properly positioned at the selected pulse point, it is operated, according to some embodiments, to apply a controlled pressure which augments transfer of arterial pulsations to a sensing nerve of the user, as shown in block 804. As described elsewhere herein, "controlled pressure" refers to pressure that is actively regulated by the device and/or by the user within defined limits, rather than being incidental or uncontrolled. According to some embodiments, the applied pressure is typically sufficient to increase the mechanical coupling between the underlying artery and nearby sensory structures, such as cutaneous or subcutaneous mechanoreceptors, thereby enhancing the perceptibility of the heartbeat-related pulsations. In some embodiments, the level of the controlled pressure comprises at least about 5 mmHg, optionally applied for a time period exceeding 20 seconds. In practical implementations, this pressure may be maintained, ramped or modulated over one or more minutes or longer, provided that user comfort, safety, and avoidance of significant blood flow occlusion are maintained. (additional details are provided elsewhere in this specification).

In some embodiments, the controlled pressure is initially increased from a low level until the user reliably feels the arterial pulsations, but is kept sufficiently low that a pain sensation is avoided during application. The level may be subjectively tuned such that the tactile sensation is noticeable and salient but not painful, sharp, or otherwise aversive. The system may be configured such that, during normal operation, pressure levels associated with pain or excessive discomfort are detected and avoided, for example by limiting the maximum allowed pressure, by monitoring blood perfusion-related signals or by responding to user input indicating discomfort. Thus, in some embodiments, the level of the controlled pressure avoids pain sensation while applying, while still ensuring that the user perceives a clear pulsation signal.

According to some embodiments, once the device is in contact and controlled pressure is being applied, a range of pressure is determined that is sufficient for the user to feel the arterial pulsations without causing substantial blood occlusion, such as disclosed in block 806. In one implementation, at least once during use of the device, the device enters a calibration mode in which, for example, the pressure applicator is driven through a sequence of incremental pressure steps or a slow ramp while the user reports, via a user interface, when the pulsations first become clearly perceptible and when the sensation becomes too strong or uncomfortable. In other implementations, the system automatically monitors signals using a sensor such as described in box 208 of FIG. 2, indicative of blood flow, such as optical signals (e.g., photoplethysmographic data), temperature, or other indices, to identify pressure levels at which arterial inflow or venous outflow is significantly compromised. According to some embodiments, by combining subjective and/or objective information, a user-specific "comfort-effective" pressure range, bounded below by a minimum level at which the user reliably perceives the pulsations and bounded above by a level beyond which pain or significant blood occlusion is likely. This determination of a range of pressure may be performed during a dedicated calibration session or dynamically updated during repeated sessions over time.

According to some embodiments, the determined pressure range is then used in a method of increasing relaxation of the user as shown in block 808. In some embodiments, the same range can be stored and reused in later sessions; in other embodiments, the range is updated or refined as the user's physiology or preferences evolve. The relaxation method may be oriented to acute-stress release, for example to quickly reduce a temporarily elevated stress level related to a specific event or situation. In other embodiments, the same method is employed for ongoing wellness maintenance, for example as part of a daily or weekly routine intended to support general emotional well-being, promote more restful sleep, or assist with recovery from chronic stress conditions. The method may employ different session types or modes, such as a brief "acute-stress relief" program and a longer "ongoing wellness" program, which may vary in overall duration, target pressure profiles, or additional instructions provided to the user.

In some embodiments, the method further comprises determining a stress level of the user prior to applying the controlled pressure, as shown in block 810. This may involve at least one objective measurement, subjective assessment or both. For example, prior to initiating a session, the user may be prompted to rate their perceived stress, anxiety, or agitation on a numerical scale (e.g., 0-10) or to select from descriptive options (e.g., "calm," "moderately stressed," "highly stressed") and/or via a voice input. Concurrently or alternatively, the device and/or a companion system may analyze physiological parameters such as heart rate, heart rate variability, respiratory rate, galvanic skin response, or other indicators of autonomic nervous system activity to derive a stress index. The resulting pre-session stress level can serve as a baseline against which relaxation effects are assessed.

According to some embodiments, following the baseline assessment, the device is again positioned, if necessary, which comprises the pressure applicator at the selected pulse point of the user, as shown in block 812. According to some embodiments, the method then includes applying a level of pressure within the previously determined range to promote relaxation of the user as shown in block 814. The initial pressure level may be selected within the middle portion of the range or may be biased upward or downward based on the pre-session stress level, user preference, or prior session history. For example, if the user reports very high stress, the method may begin at a somewhat higher pressure within the acceptable window (i.e., perceivable range, preferably not causing health risks such as substantial blood occlusion) to ensure strong salience of the tactile signal; if the user is only mildly stressed or wishes a gentler experience, the method may use a lower level within the same range. In some embodiments, the pressure is then held substantially constant for at least about 20 seconds or longer, while in other embodiments the pressure is modulated according to time-varying patterns (e.g., gentle oscillations within the range) to support attentional engagement.

According to some embodiments, during the relaxation session, the method may include directing attention of the user to a tactile sensation produced by the controlled pressure. In one embodiment, the user is verbally or textually instructed to bring awareness to the pulse sensation at the contact site and to "follow" the rhythm of their heartbeat as it is conveyed through the device. In additional embodiments, the system employs one or more sensory cues to help the user orient and maintain attention. For example, the system may use an audio signal (such as a voice prompt, tone, chime, or rhythmic sound) to remind the user to notice the tactile pulsations and to pair these sensations with slow breathing. Alternatively or additionally, an optical signal (such as a flashing or pulsing light on the device, a visual prompt on a smartphone display, or a color change) may be synchronized with or associated with the pressure pattern. In yet other embodiments, a haptic signal (e.g., an additional vibration or tapping stimulus) may be applied adjacent to, or at a different location than, the primary pressure applicator to reinforce the perception of rhythmicity and to cue the user to attend to the sensation. Such audio, optical and/or haptic signals displays (collectively referred to as sensory cues) can be initiated at the beginning of a session, at periodic intervals, and/or adaptively based on detected lapses in the user's engagement.

In further embodiments, during or following application of the level of pressure within the determined range, the method includes again determining a stress level of the user as shown in block 816. The determination stress level may be assessed using the same subjective and/or objective techniques described above. For example, after several minutes of controlled pressure, the user may be asked to re-rate their stress or relaxation on the same scale used at baseline, and/or the system may analyze updated physiological data to derive a second stress index. The difference between the pre-application and post-application stress levels provides an indication of the degree of relaxation achieved and may be stored as part of a session log.

In some embodiments, the method further comprises adjusting the level of the controlled pressure based on the stress level as shown in block 818. In one scenario, if the stress level does not decrease as expected, or decreases only slightly after a given interval, the system may automatically adjust the applied pressure within the previously established safe and effective range to seek a more favorable point. For example, during an ongoing session, the pressure may be gradually increased (within the upper bound of the range) if the user remains highly stressed, in order to enhance the tactile salience and strengthen the association between the heartbeat sensation and relaxation cues. Conversely, if the user reports marked relaxation, drowsiness, or if physiological indicators suggest a low stress state, the system may reduce the pressure toward the lower bound of the range while still maintaining perceptibility. It is suggested that maintaining a reduced, but still perceptible, pressure allows ongoing tactile awareness of the pulse to help sustain the relaxation state and prevent abrupt loss of the calming stimulus that could otherwise diminish the relaxation response. In manual modes, the user may themselves adjust the pressure, guided by prompts such as "increase slightly if you do not yet feel the pulse clearly" or "decrease if the sensation becomes too strong," thereby informally titrating the stimulus in relation to their own stress level.

In some embodiments, the method further comprises monitoring the arterial pulsations while the pressure is being applied. This monitoring can be performed by one or more sensors integrated in or near the pressure applicator, such as an optical sensor, mechanical sensor, or other detector. Monitoring can confirm that pulsations remain present and within an expected amplitude range, thereby affirming that the artery remains patent and that substantial blood occlusion has not occurred. The system may optionally adjust the level of the controlled pressure based on the monitored arterial pulsations. For example, if pulsation amplitude decreases below a threshold consistent with excessive compression or occlusion, the device may automatically reduce the applied pressure to restore adequate flow and pulsation amplitude. Alternatively, if the pulsations become overly strong or irregular within the monitored signal, the device may adapt the pressure pattern to maintain comfort and safety while preserving the desired sensory effect.

In some embodiments, the method also includes reducing the level of the controlled pressure if a predetermined level of relaxation is reached and/or if an indication of blood flow occlusion is detected. For example, if the pre- and post-application stress indices indicate that the user has reached a target relaxation level, or if a user-specified goal (e.g., a stress rating reduced by at least three points on a numerical scale) is met, the device may gradually ramp down the pressure to a minimal or zero level, optionally over tens of seconds to avoid sudden changes. Likewise, if the monitored arterial pulsations indicate a pattern suggestive of occlusion (e.g., loss of pulsation signal, sharp change in waveform morphology) or if the user reports numbness or discomfort, the device can respond immediately by lowering the pressure and/or signaling the user to reposition or pause the session. Reduction in pressure under these conditions promotes both safety and a gentle transition from the more intense part of the relaxation procedure back toward baseline tactile input.

The method may be terminated under one or more conditions, such as completion of a pre-specified session duration, attainment of a target relaxation level, or user-initiated stop input such as shown in block 820. According to some embodiments, the system may log the initial and final stress levels, pressure settings, pulse-point location used (e.g., thumb, finger, wrist, ankle or temple), duration, and any significant adjustments made during the session. This information can be used by a controller of the wearable device or by an associated external computing device (such as a paired smartphone or cloud server) to, for example, refine subsequent sessions, enable personalization of future pressure ranges or pressure-adjustment strategies, and/or provide summaries to the user or a caregiver regarding the effectiveness of the intervention over time.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of increasing perception of self-heartbeats by a user, the method comprising:

mounting a wearable device against a pulse point of the user, said wearable device comprising a pressure applicator;

using said device to apply said controlled pressure at a level sufficient to augment transfer of arterial pulsations corresponding to the self-heartbeats from an artery to a sensing nerve of the user and improve the perception of self-heartbeats by the user without causing substantial blood occlusion.

2. The method of claim 1, wherein said controlled pressure is at a level and/or duration which promote relaxation of the user.

3. The method of claim 1, wherein said level comprises at least 5 mmHg optionally for a time period exceeding 20 seconds.

4. The method of claim 1, further comprising determining a stress level of the user prior to and/or following applying, optionally the method further comprises adjusting said level of said controlled pressure based on said stress level.

5. The method of claim 1, further comprising directing attention of the user to a tactile sensation produced by said controlled pressure, optionally wherein said directing attention is by an audio signal, optical signal and/or haptic signal.

6. The method of claim 1, wherein said applicator is operated by the user.

7. The method of claim 1, wherein said device is automatically operated.

8. The method of claim 1, wherein said promoting relaxation is for acute-stress release.

9. The method of claim 1, wherein said promoting relaxation is for ongoing wellness maintenance.

10. The method of claim 1, wherein said skin region comprises a pulse point, optionally selected from a group consisting of a thumb, a finger, a wrist, an ankle and a temple.

11. The method of claim 1, further comprising monitoring the arterial pulsations and optionally adjusting said level of controlled pressure based on the monitored arterial pulsations.

12. The method of claim 1, further comprising reducing said level of said controlled pressure if a pre-determined level of relaxation is reached and/or an indication of the blood flow occlusion is indicated.

13. The method of claim 1, wherein said controlled pressure, is, at least in part, under control of an application downloadable from an application store or application marketplace optionally executable on a computing platform associated with the wearable device, the application being configured to control one or more operating parameters of the pressure applicator.

14. The method of claim 1, wherein said wearable device comprises:

(i) a body sized and shaped for mounting against a pulse point of the user, said body including:
at least one integrated deforming section;

(ii) a regulator which regulates said deforming section to cause said body to apply controlled pressure such that the user perceives the self-heartbeats over a predetermined period of time.

15. The method of claim 14, wherein said deforming section comprises at least one actuator selected from a group consisting of a pneumatic chamber, a hydraulic chamber and a shape memory alloy actuator.

16. The method of claim 14, wherein said device comprises at least one sensor, optionally selected from a group consisting of a safety sensor, a physiological sensor and an operability sensor.

17. The method of claim 16, wherein said regulator is configured to regulate said pressure in response to physiological data received from said physiological sensor.

18. The method of claim 14, wherein said device further comprises an actuator that generates a human perceptual signal corresponding to said self-heartbeats.

19. The method of claim 16, wherein said body comprises a decompression section which comprises a circuitry controlled by said regulator in response to said regulator receiving a signal from said sensor and/or said user.

20. The method of claim 14, wherein said regulator comprises a calibration mode configured for determining a personalized range of said controlled pressure based on at least one of a user preference and a safety parameter comprising blood flow.

* * * * *